United States Patent [19]

Spangler

[11] Patent Number: 4,523,333
[45] Date of Patent: Jun. 18, 1985

[54] DISPOSABLE BIB HAVING TAPE-TAB FASTENER

[75] Inventor: Richard A. Spangler, Cincinnati, Ohio

[73] Assignee: The Procter & Gamble Company, Cincinnati, Ohio

[21] Appl. No.: 549,370

[22] Filed: Nov. 4, 1983

[51] Int. Cl.³ .................... A41B 13/10; A41D 13/04
[52] U.S. Cl. .................................... 2/49 R; 604/390
[58] Field of Search .................... 2/49 R, 50, 51; 604/390, 389, 386

[56] References Cited

U.S. PATENT DOCUMENTS

| | | | |
|---|---|---|---|
| 2,902,734 | 9/1959 | Walters | 24/7 |
| 3,001,646 | 9/1961 | Cooper | 2/49 R X |
| 3,257,677 | 6/1966 | Batchelder et al. | 12/142 |
| 3,329,969 | 7/1967 | Farber et al. | 2/49 R |
| 3,416,157 | 12/1968 | Marder et al. | 2/49 |
| 3,867,940 | 2/1975 | Mesek | 128/287 |
| 3,955,576 | 5/1976 | Safford | 128/287 |
| 4,029,098 | 6/1977 | Karami | 604/390 |
| 4,047,528 | 9/1977 | Karami | 604/390 |
| 4,068,665 | 1/1978 | Nelson | 128/287 |
| 4,100,921 | 7/1978 | Schaar | 128/284 |
| 4,186,744 | 2/1980 | Ness | 604/390 |
| 4,210,144 | 7/1980 | Sarge | 128/287 |
| 4,378,800 | 4/1983 | Schaar | 604/390 |
| 4,416,025 | 11/1983 | Moret et al. | 2/49 R |
| 4,445,231 | 5/1984 | Noel | 2/49 R |

FOREIGN PATENT DOCUMENTS 2035053  6/1980  United Kingdom ............... 604/390

*Primary Examiner*—Louis K. Rimrodt
*Assistant Examiner*—J. L. Kravitz
*Attorney, Agent, or Firm*—Thomas J. Slone; Fredrick H. Braun; Richard C. Witte

[57] ABSTRACT

A disposable bib of flexible sheet material having a neck-accommodating aperture, a predetermined line-of-parting which extends from the edge of the aperture to an adjacent outer edge of the bib, and a tape-tab fastener having pressure sensitive adhesive coated ends. The tape-tab fastener is, until time-of-use, wholly disposed on the back surface of the bib adjacent the line-of-parting. At time-of-use, the line-of-parting is parted; and a mother's-bond portion of the tape-tab fastener is peeled from the factory-bond portion of the fastener, extended to bridge the parted line-of-parting, and then secured to a predetermined mother's-bond zone of the front surface of the bib. The line-of-parting provides structural integrity for the bib prior to use, yet enables the bib to be fitted on an infant at the time of use. In a preferred embodiment, the line-of-parting is a tearable line-of-weakening comprising a plurality of spaced cuts or perforations. In another embodiment, the line-of-parting is a line-of-severance that is bridged by the factory-bond portion of the tape-tab fastener prior to time-of-use of the bib.

9 Claims, 15 Drawing Figures

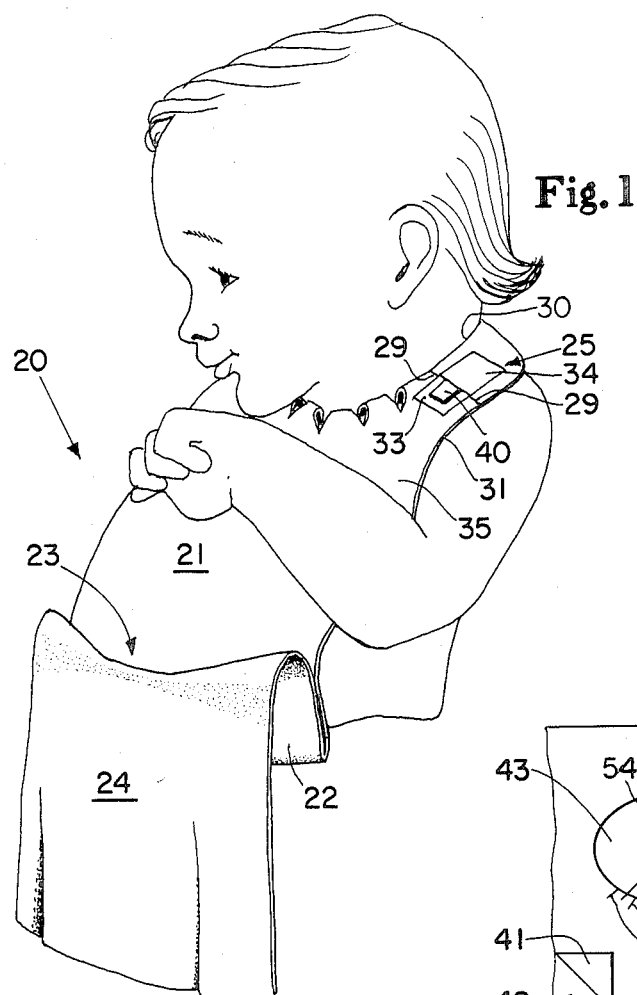
Fig. 1
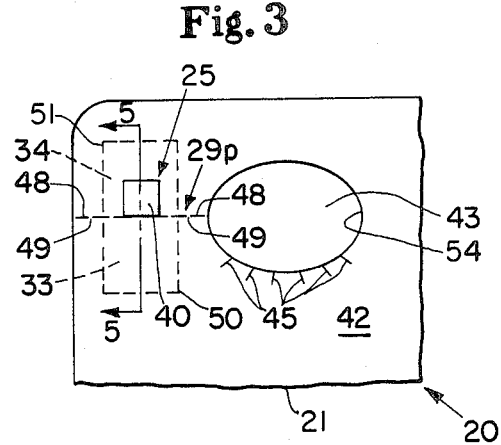
Fig. 2
Fig. 3

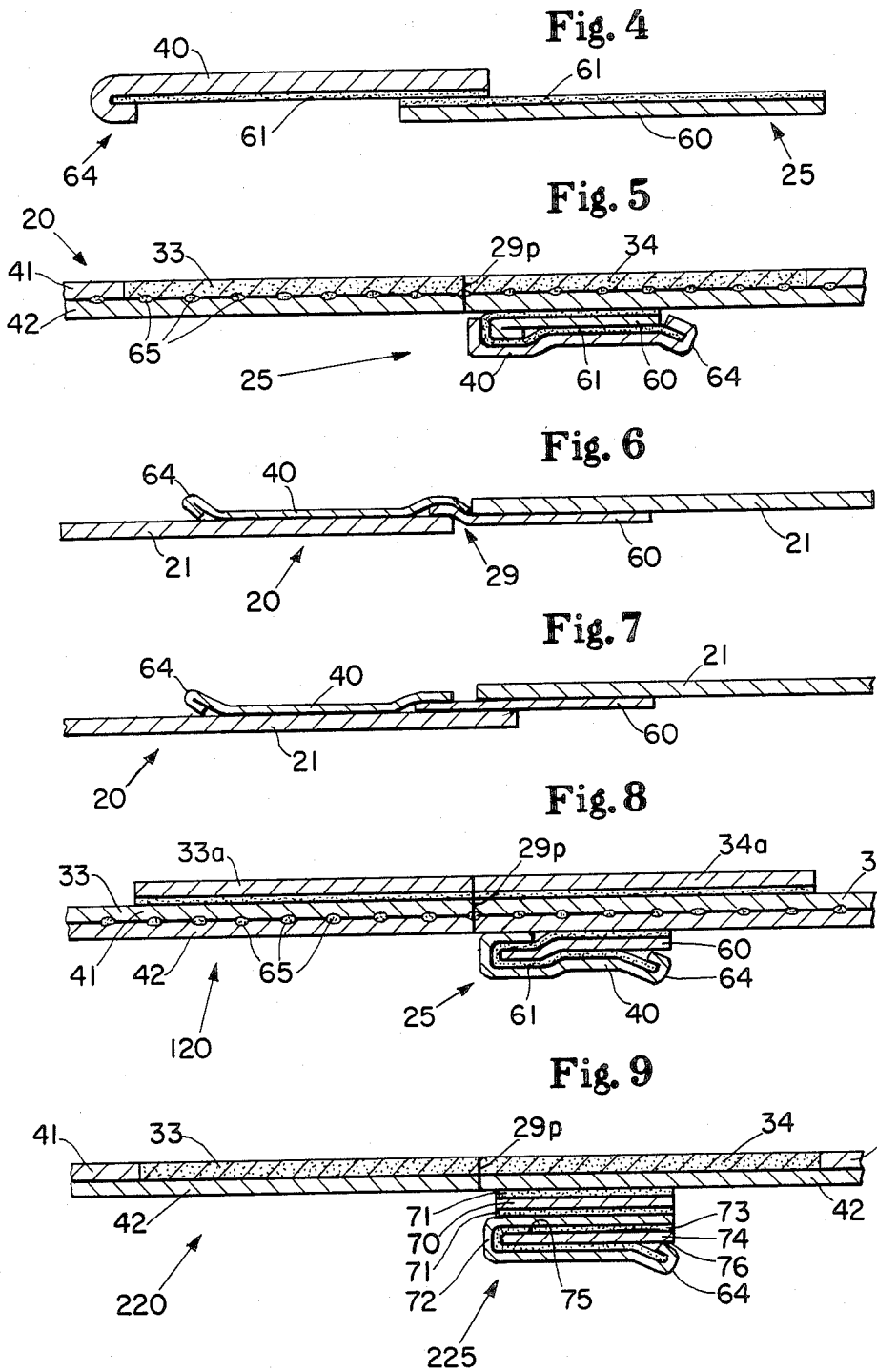

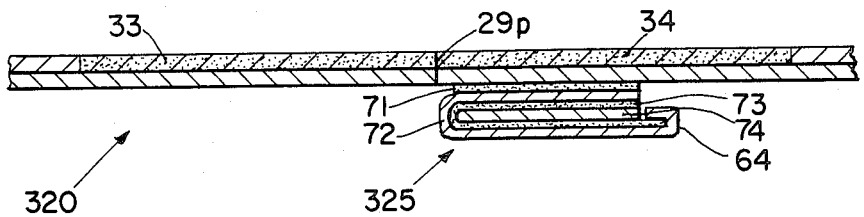
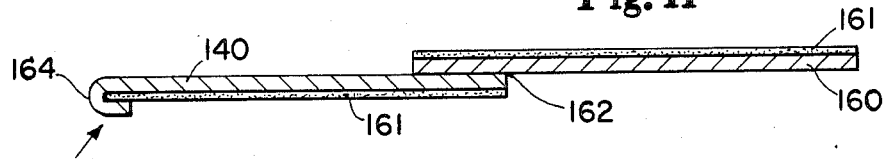
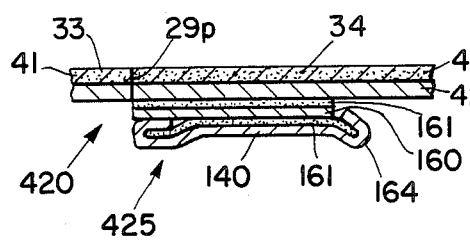
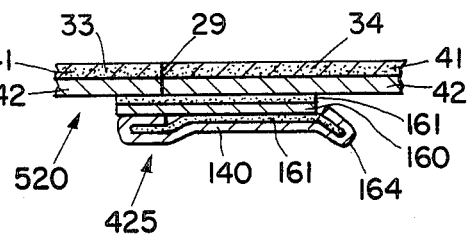
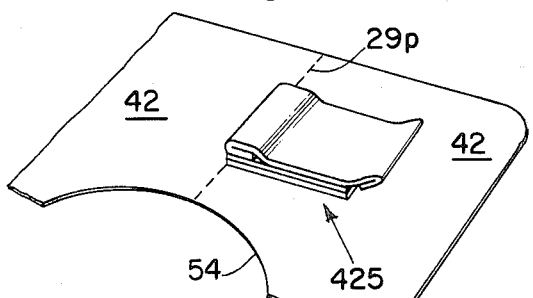
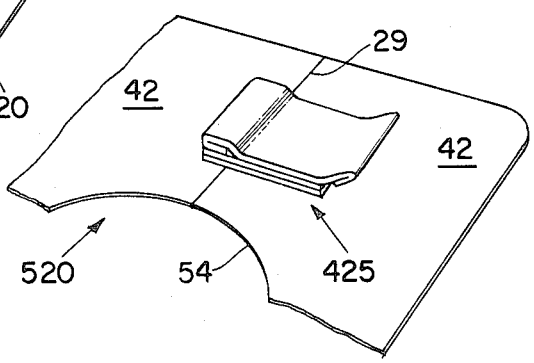

DISPOSABLE BIB HAVING TAPE-TAB FASTENER

TECHNICAL FIELD

This invention pertains to disposable garments such as bibs or aprons or the like which are fitted with tape-tab fasteners. More particularly, it pertains to disposable bibs having a tape-tab fastener which is factory applied to the back surface of the bib; and which fasteners comprises a mother's-bond end which, at-time-of-use, is peeled from the factory-bond end and applied to a front surface area of the bib; ie, a mother's-bond area or region of the front surface of the bib.

BACKGROUND ART

U.S. Pat. No. 3,416,157 which issued Dec. 17, 1968 to H. L. Marder et al discloses a disposable bib, FIG. 5, which comprises a tape-tab fastener having both ends secured to front surface areas of the bib. Additionally, this patent discloses coating surface areas of the bib with adhesives which are preferably cohesive in nature: adhesive substances which stick only to themselves and have substantially no adhesion for other surfaces. Thus, with such contact adhesives, such coated areas are in fact the adhesive elements which cooperate with each other to secure the bib on a user. As such, they are alternatives to tape-tab fasteners of the type having pressure sensitive adhesive on their end tabs.

U.S. Pat. No. 2,902,734, which issued Sept. 8, 1959 to B. G. Walters discloses a Napkin Fastening Means which is shown to be U-folded—adhesive-to-adhesive—prior to use; and which, in use, has one end secured to the napkin and the other end applied to, for example, a portion of the user's garment. This fastener has a U-folded grasping portion on one end which is imprinted PULL; and has the other end U-folded and imprinted HOLD.

U.S. Pat. No. 3,955,576 which issued May 11, 1976 to Robert D. Safford, and U.S. Pat. No. 4,100,921 which issued July 18, 1978 to Charles H. Schaar, and U.S. Pat. No. 4,378,800 which issued Apr. 5, 1983 to Charles H. Schaar disclose disposable diaper constructions having U-folded tape-tab fasteners which are factory applied to one surface (eg, the surface which faces inwardly towards the user) of their respective diaper constructions; and which, in use, have mother's-bond ends which are applied to mother's-bond regions on their opposite surfaces.

U.S. Pat. No. 4,068,665 which issued Jan. 17, 1978 to Lawrence E. Nelson discloses a disposable diaper construction which comprises a U-folded tape-tab fastener having its factory-bond end secured intermediate facing regions of the topsheet and the backsheet of the diaper, and which is U-folded upon manufacture so that its mother's-bond end overlies the factory-bond end with a portion of the topsheet and a segment of a release liner disposed therebetween.

U.S. Pat. No. 3,257,677 which issued June 28, 1966 to C. F. Batchelder et al discloses a Releasable Attaching Device which, as shown in FIG. 1, comprises a tape having adhesive coatings on oppositely facing end regions; and FIG. 2 illustrates a modified form of the invention wherein both surfaces of the tape are coated with adhesive, and opposite end portion's are fitted with cover "patches". As disclosed, the releasable attaching device is utilized to temporarily attach an insole to a shoe last.

U.S. Pat. No. 3,867,940 which issued Feb. 25, 1975 to Frederick K. Mesek et al discloses a Scrim Reinforced Disposable Diaper wherein scrim is laminated to the backsheet for reinforcement thereof in the tape attachment region and other regions; and U.S. Pat. No. 4,210,144 which issued July 1, 1980 to Henry D. Sarge et al discloses a Disposable Diaper Having Refastenable Tape System wherein the backsheet of the diaper is reinforced by a coating comprising a self-adhering coating material having a relatively high tensile strength and a low elongation to tensile force property relative to the backsheet.

DISCLOSURE OF THE INVENTION

In accordance with one aspect of the invention, a disposable bib is provided which comprises a body panel having a neck-accommodating aperture, means defining a line-of-parting extending between the edge of the aperture and an adjacent outer edge of the bib, and a tape-tab fastener. The tape-tab fastener comprises a factory-bond end and a mother's-bond end. The factory-bond end is adhered by adhesive thereon to the back surface of the bib adjacent the line-of-parting. The fastener is configured and disposed to enable extending said mother's-bond end across the line-of-parting after it has been parted, and to adhere it with adhesive thereon to a mother's-bond area of the front surface of the bib. The body panel is preferably a laminate comprising an absorbent topsheet lamina of, for example, low-strength tissue paper; and an impervious backsheet lamina of, for example, polyethylene film. The mother's-bond area of the bib may be reinforced by an overlying landing pad of a flexible sheet material adhered thereto, or by impregnating it and the underlying zone of the topsheet with a bonding material such as a non-pressure sensitive adhesive. The tape fastener is, preferably, a two piece assemblage of the same tape material wherein two pieces are bonded together with a lap joint. The tape is provided with pressure sensitive adhesive on one surface and with a release coating or other release means on its other surface. In one embodiment, the two pieces of tape are bonded together with overlapping areas of their adhesive coated surfaces; and, in another embodiment, the tapes are bonded together with end portions of their release surfaces in face-to-face relation. In one aspect of the invention, the line-of-parting is an unbroken line-of-severance in the body panel of the bib, and the fastener is so disposed that its factory-bond end bridges the line-of-severance prior to use of the bib.

BRIEF DESCRIPTIONS OF THE DRAWINGS

While the specification concludes with claims which particularly point out and distinctly claim the subject matter regarded as forming the present invention, it is believed the invention will be better understood from the following description taken in conjunction with the accompanying drawings in which:

FIG. 1 is a perspective view of a disposable bib embodiment of the present invention.

FIG. 2 is an enlarged scale, frontal plan view of a fragmentary portion of the disposable bib of FIG. 1.

FIG. 3 is an enlarged scale, rear plan view of the fragmentary portion of the disposable bib shown in FIG. 2 except FIG. 3 depicts the structure in its prior-to-use (ie, factory/shipping) configuration.

FIG. 4 is an edge view of a two-piece tape-tab fastener assemblage wherein face-to-face adhesive coated end areas are lap jointed together by their adhesive coatings, and one end of which is U-folded to form a grasping portion.

FIG. 5 is a fragmentary sectional view taken along line 5—5 of FIG. 3.

FIG. 6 is a fragmentary sectional view taken along line 6—6 of FIG. 2.

FIG. 7 is a fragmentary sectional view similar to FIG. 6 except the joint effected by the tape-tab fastener in FIG. 7 is an overlapping joint: ie, portions of the body panel of the bib are disposed in overlapping relation in FIG. 7.

FIG. 8 is a fragmentary sectional view similar to FIG. 5 except the topsheet lamina of the FIG. 8 bib construction is reinforced with segments of reinforcing sheet material adhered to the top surface thereof.

FIGS. 9 and 10 are sectional views which are similar to FIG. 5, and which show alternate tape-tab fastener configurations.

FIG. 11 is an edge view similar to FIG. 4 which shows an alternate embodiment of a two-piece tape-tab fastener having a lap joint of bonded end areas of the release surfaces of the tape segments.

FIGS. 12 and 13 are fragmentary sectional and perspective views, respectively, of a bib embodiment of the present invention wherein the closed end of the U-folded tape-tab fastener is disposed subjacent a tearable line-of-weakening through the left shoulder region of the bib.

FIGS. 14 and 15 are fragmentary sectional and perspective views, respectively, of a bib embodiment of the present invention wherein the factory-bond end of the tape-tab fastener bridges an unbroken line-of-severance in the left shoulder region of bib.

DETAILED DESCRIPTION OF THE INVENTION

An exemplary disposable bib 20 embodying the present invention is shown in perspective in FIG. 1 to comprise a body panel 21, a pocket panel 22 which extends the full width of the body panel to form a full-width pocket 23, an apron panel 24 which pendulously depends from the top edge of the pocket panel 22, and a tape-tab fastener 25 which bridges a line-of-severance 29 which extends between the edge 30 of a neck-aperture in the body panel 21 and an adjacent outer edge 31. Additionally, bib 20 is shown to have reinforced areas 33 and 34 disposed adjacent the line-of-severance 29. The reinforced area 33 is designated the mother's-bond area of the front surface 35 of body panel 21, and has the visible portion of tape-tab fastener 25 adhered thereto. The portion of tape-tab fastener 25 which is visible in FIG. 1 is designated the mother's-bond end 40.

A left shoulder fragment of bib 20 is shown in enlarged scale in FIG. 2. Body panel 21 is shown to be a laminate comprising a topsheet lamina 41 and a backsheet lamina 42. In an exemplary embodiment of bib 20, lamina 41 comprises a sheet of high bulk, absorbent tissue paper having a basis weight of about twenty-two (22) pounds per three-thousand square feet (about 35.9 grams per square meter) and a nominal caliper of about fourteen (14) mils (about 0.36 mm.); backsheet lamina 42 comprises a polyethylene film having a nominal thickness of about one mil (about 0.0254 mm); and the laminae are preferably secured together with a pattern of discrete areas bonded together with, for example, National Starch Co. adhesive number NS 34-2857. As also indicated in FIG. 2, the neck-accommodating aperture is designated 43 having edge 54; and a portion of the body panel 21 disposed adjacent edge 54 is shown to be subdivided into a plurality of cantilevered petals 44 by cuts 45 which extend radially outwardly from edge 54 to provide comfortable conformance to the user's neck when the bib is applied as shown in FIG. 1.

FIG. 3 is a back view of the left shoulder of bib 20 shown in FIG. 2. However, FIG. 3 depicts the fragment in its factory state; its state upon completion of its manufacture. Thus, whereas bib 20 is shown in FIGS. 1 and 2 to have a broken line-of-severance 29, bib 20 is shown in FIG. 3 to have a line-of-parting 29p comprising a plurality of cuts 48 which are spaced by uncut portions 49. The dotted lines 50 and 51 are the lineaments of the reinforced areas 33 and 34, respectively, FIG. 2, of the topsheet lamina of the bib. In FIG. 3, the tape-tab fastener 25 is shown to be disposed on the back surface of backsheet lamina 42 subjacent reinforced area 34, and with one end disposed adjacent line-of-parting 29p. The portion of fastener 25 which is visible in FIG. 3 in the mother's-bond end 40 as will be more apparent after describing FIG. 5, below.

FIG. 4 is an edge view of tape-tab fastener 25 prior to its being U-folded and applied to the back surface of bib 20. As shown, fastener 25 is an assembly of two pieces to tape: the mother's-bond end or element 40 and the factory-bond end or element 60. Fastener elements 40 and 60 are preferably but not necessarily made from the same tape stock which is coated with pressure sensitive adhesive 61 on one surface and which comprises means for its other surface to have a release property relative to adhesive 61. In the configuration shown in FIG. 4, the distal portion of the mother's-bond element 40 of fastener 25 is U-folded to provide a grasping portion 64; and the fastener elements 40 and 60 are lap jointed by the adhesive 61 on their overlapped proximal end portions. Exemplary tape stocks for making fasteners 25 have been obtained from Anchor Continental, Inc., Columbia, S.C. and designated by Anchor as Adhesive Tape Types 503X and 503S. The 503X Tape has more aggressive adhesive than the 503S tape, and has been utilized for bibs having mother's-bond regions impregnated with Petrothene NA601-00 as described below; and the 503S tape has been found to be satisfactory for bibs having polyethylene landing pads as described below in conjunction with describing alternate bib 120, FIG. 8.

FIG. 5 is a fragmentary sectional view along line 5—5 of FIG. 3, and in which the thicknesses of the members have been greatly exaggerated to clearly show their functional features. FIG. 5 shows a fragment of bib 20 having a tape-tab fastener 25, FIG. 4, U-folded and adhered to the outer surface of backsheet 42 subjacent reinforced area 34, and with the closed end of the U disposed adjacent the line-of-weakening 29p. As also shown in FIG. 5, the topsheet lamina 41 and the backsheet lamina 42 are secured together with spaced areas of adhesive 65. It is, however, not intended to thereby limit the means for laminating to adhesive per se; nor it is intended to limit the invention to only laminated structures per se.

Still referring to FIG. 5, the reinforced zones or areas 33 and 34 of topsheet 41 are impregnated with a bonding material: such as, for example, Petrothene NA 601-00 from U.S.I. Chemicals Company, or Eastobond A-3 from Eastman Adhesive. Such bonding materials are applied to area 33 in sufficient quantity to enable operative attachment of the mother's-bond end 40 of tape-tab 25 thereto. That is, lamina 41 of suitable basis weight and bulk paper have insufficient inherent strength to enable operative attachment thereto of tape-tab end 40 thereto: ie, with sufficient strength to withstand forces imposed by applying the bib to a wearer and during the normal usage of the bib. Therefore, area 33 of lamina 41 is sufficiently impregnated with bonding material to enable the mother's-bond tape joint to withstand the rigors of application and use: ie, operative attachment. Area 34 is similarly impregnated so that the factory-bond region of the body panel is sufficiently strong to withstand the rigors of application and use of the bib even though the factory-bond end of fastener 25 is not secured to area 34 per se. Additionally, it is preferable to sufficiently impregnate areas 33 and 34 with bonding material to form a continuum of bonding material from the top surface of lamina 41 to the front surface of lamina 42 so that the strength property of the backsheet lamina 42 is added—at least in part—to the strength of the impregnated areas. The impregnating bonding material may effect such a continuum directly with the front surface of lamina 42, or through the zones 65 of laminating adhesive, or both as indicated in FIG. 5.

FIG. 6 is a fragmentary sectional view taken along line 6—6 of FIG. 2: bib 20 after the mother's-bond end 40 has been peeled from its FIG. 5 position, and adhered to the front surface of area 33. However, whereas all of the laminae and layers of tape substrate and adhesive are shown in FIG. 5—ie, the same structure prior to applying it to a user—FIG. 6 depicts the laminate and the tape ends as single layer structures to substantially lessen the distortion induced by the exaggerated thicknesses of the several layers. Thus, FIG. 6 shows a butt type joint between the portions of body panel 21 which are adjacent line-of-severance 29.

FIG. 7 is a fragmentary sectional view similar to FIG. 6 except, in FIG. 6, the adjacent portions of body panel are positioned in overlapping relation as it might be when bib 20 is applied to a relatively small user.

FIG. 8 is a fragmentary sectional view of a fragmentary portion of an alternate bib construction designated 120 similar to FIG. 5 except the FIG. 8 structure has discrete landing pads 33a and 34a of sheet material applied to the front surface areas 33 and 34, respectively, of topsheet lamina 41 for reinforcement thereof rather than the impregnating described above. Exemplary landing pads may be made from one mil polyethylene, a film which has a satisfactory release property with respect to the adhesive on the Anchor Tape Type 503S identified above.

FIG. 9 is a fragmentary sectional view similar to FIG. 5 which shows a fragmentary left shoulder portion of an alternate bib 220 having an alternate tape-tab fastener 225. But for the alternate fastener 225, alternate bib 220 is preferably the same as bib 20, FIG. 1. Accordingly, only alternate fastener 225 will be described to avoid a redundant description of the body panel 21 of bib 220. Alternate fastener 225 comprises a segment of double-faced adhesive tape 70 having an adhesive coating 71 on each surface; a U-folded segment of a single-faced adhesive tape 72 having an adhesive coating 73 on one surface thereof; and a segment of a release tape 74 having one surface 75 to which adhesive 73 has a substantially higher affinity than its other surface 76 which has a release property with respect to adhesive 73. To apply bib 220 to a user, line-of-parting 29p is parted, and the distal portion of tape 72 is peeled from release surface 76 of tape 74. This distal portion of tape 72 is the mother's-bond end of the fastener and is applied the same as the mother's-bond end 40 of bib 20 as described above and as shown in FIGS. 1, 2, and 6.

FIG. 10 is a fragmentary sectional view similar to FIG. 9 but which shows another alternate bib 320 which comprises alternate tape-tab fastener 325 and which is otherwise the same as bib 220, described above. Alternate tape-tab fastener 325 is like fastener 225, FIG. 9 except its single-sided, U-folded tape 72 is adhered directly to the back surface of the bib 320 with adhesive 371 rather than using two-sided tape 70 for that purpose. Fastener 325 is used in the same way as Fastener 225 described above.

FIG. 11 is an edge view similar to FIG. 4 which shows an alternate tape-tab fastener 425 which preferably comprises two lengths of the same single-sided tape stock: a mother's-bond length 140 having one end U-folded to form grasping portion 164; and a factory-bond length 160. Both lengths 140 and 160 are coated with adhesive 161 on their oppositely facing surfaces; and their other surfaces have a release property with respect to adhesive 161. Lengths 140 and 160 have overlapping portions of their release surfaces bonded together: for example, for thermoplastic tape embodiments, they may be thermobonded or ultrasonically bonded as indicated by designator 162. Fastener 425 is U-folded to adhere the adhesive coated surface of the mother's-bond length 140 to the release surface of the factory-bond length 160; and applied to the back surfaces of bib constructions as described below. However, whereas the two-element tape-tab fastener 25 is easier to make and handle than a single piece of tape having oppositely facing end portions coated with adhesive, the fastener 425 provides the additional benefit of being able to use the entire coated areas of both tape lengths (but for the nominal length used to form grasping portion 164) for adhering the lengths to surface areas of the bib. Thus, the tape lengths of fastener 425 may be made shorter than those of fastener 25 by an amount equal to the length of the overlapped areas for fasteners having equal fastening power: ie, equal areas of adhesive available for securement to bib surfaces.

Alternate bib 420, FIGS. 12 and 13, and alternate bib 520, FIGS. 14 and 15, comprise a tape-tab fastener 425, FIG. 11, which has been U-folded and adhered by adhesive 161 to the back surface of its respective bib. Fastener 425 is disposed on bib 420 with the closed end of its U-shape disposed subjacent the line-of-parting 29p: ie, a line-of-weakening comprising spaced cuts as shown in FIG. 3. Fastener 425 is disposed on bib 520 with the closed end of its U-shape disposed to the left of the unbroken line-of-severance 29, and with its major portion disposed to the right of line-of-severance 29 as viewed in FIG. 14. The factory-bond end 160 of fastener 425 bridges the line-of-severance 29 upon being so applied during its manufacture. Thus, the bridged line-of-severance 29 constitutes a line-of-parting which is parted by peeling the left portion of the body panel of the bib, as viewed in FIG. 14, from the subjacent proximal portion of the factory-bond end 160 of fastener 25.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A disposable bib comprising a body panel having a neck-accommodating aperture, means defining a predetermined manually partable line-of-parting extending between the edge of said aperture and an adjacent outer edge of said body panel, and a tape-tab fastener, said line-of-parting being disposed and configured to, when parted, enable the portions of said bib disposed adjacent the opposite sides of said line-of-parting to be spread apart to enable fitting said bib about the neck of the user, said fastener comprising a factory-bond end and a mother's-bond end, said factory-bond end being adhered by adhesive thereon to the back surface of said bib adjacent said line-of-parting, said fastener being configured and disposed to enable extending said mother's-bond end across said line-of-parting when parted and adhering it by adhesive thereon to a mother's-bond area of the front surface of said bib, said line-of-parting being an unbroken line-of-severance through said body panel, and said factory-bond end of said fastener comprising a distal portion and a proximal portion, said fastener being so disposed prior to parting said line-of-parting, that said proximal portion and said distal portion are disposed on opposite sides of said line-of-parting, said bib further comprising means for said proximal portion to be peelable from said back surface of said bib whereby said line-of-parting may be parted by peeling said proximal portion from said back surface of said bib.

2. The disposable bib of claim 1 wherein said body panel comprises a flexible laminate comprising an absorbent topsheet lamina and a liquid impervious backsheet lamina, said topsheet lamina comprising a fibrous sheet having an insufficient inherent strength property to enable operative securement thereto of said mother's-bond end of said fastener, said bib further comprising means for sufficiently increasing the strength property of said mother's-bond region to enable operative securement thereto of said mother's-bond end of said fastener.

3. The disposable bib of claim 2 wherein said means for increasing the strength property of said mother's-bond region comprises impregnating said mother's-bond region of said topsheet lamina with an interfiber bonding material.

4. The disposable bib of claim 3 wherein said impregnating and said bonding material render said mother's-bond end of said fastener refastenable to said mother's-bond region of said topsheet lamina.

5. The disposable bib of claim 3 wherein said interfiber bonding material comprises means for effecting a continuum of said bonding material from the front surface of said topsheet lamina to the front surface of subjacent portions of said backsheet lamina.

6. The disposable bib of claim 5 wherein said impregnating and said bonding material render said mother's-bond end of said fastener refastenable to said mother's-bond region of said topsheet lamina.

7. The disposable bib of claim 2 wherein said means for increasing the strength property of said mother's-bond region comprises a landing pad of sheet material adhered to the front surface of the mother's-bond region of said topsheet lamina, said landing pad being greater in area than said mother's-bond end of said fastener and having an outwardly facing surface to which said mother's-bond end of said fastener will operatively adhere.

8. The disposable bib of claim 1 wherein said tape-tab fastener comprises two lengths of a tape comprising a flexible thermobondable substrate having a pressure sensitive adhesive coating on a first surface thereof, and the other surface of which has a release property relative to said pressure sensitive adhesive, each said other surface comprising an end portion and a remainder portion, said pieces of tape being denominated a factory-bond element and a mother's-bond element and adhered together with a thermobonded lap joint comprising said end portions of said other surfaces of the two said pieces of tape thermobonded together in face-to-face relation, said fastener being folded until time of use with said adhesive coated first surface of said factory-bond element secured by said adhesive thereon to said back surface of said bib, and with the distal portion of said adhesive coated first surface of said mother's-bond element peelable adhered by said adhesive thereon to said remainder portion of said other surface of said factory-bond element.

9. The disposable bib of claim 1 wherein said tape-tab fastener comprises two lengths of a tape which tape comprises a flexible substrate having a pressure sensitive adhesive coating on a first surface thereof and the other surface of which has a release property relative to said pressure sensitive adhesive, each said first surface comprising an end portion and a remainder portion, said two lengths of tape being denominated a factory-bond element and a mother's-bond element and adhered together with a lap joint comprising said end portion of each of the two said lengths of tape bonded together by their facing areas of said pressure sensitive adhesive coatings, said fastener being folded until time of use with the said remainder portion of said first surface of said factory-bond element secured to said back surface of said bib, and with the remainder portion of said first surface of said mother's-bond element peelably adhered by said adhesive thereon to said other surface of said factory-bond element.

* * * * *